(12) United States Patent
  Ishihara

(10) Patent No.: US 12,586,231 B2
(45) Date of Patent: Mar. 24, 2026

(54) POSTURE ESTIMATION APPARATUS, POSTURE ESTIMATION METHOD, AND COMPUTER-READABLE RECORDING MEDIUM

(71) Applicant: NEC Corporation, Tokyo (JP)

(72) Inventor: Kenta Ishihara, Tokyo (JP)

(73) Assignee: NEC CORPORATION, Tokyo (JP)

( * ) Notice: Subject to any disclaimer, the term of this patent is extended or adjusted under 35 U.S.C. 154(b) by 312 days.

(21) Appl. No.: 18/273,431

(22) PCT Filed: Jun. 3, 2021

(86) PCT No.: PCT/JP2021/021140
  § 371 (c)(1),
  (2) Date: Jul. 20, 2023

(87) PCT Pub. No.: WO2022/254644
  PCT Pub. Date: Dec. 8, 2022

(65) Prior Publication Data
  US 2024/0119620 A1     Apr. 11, 2024

(51) Int. Cl.
  *G06T 7/70*     (2017.01)
  *A61B 5/00*     (2006.01)
  *A61B 5/11*     (2006.01)
  *G06T 7/50*     (2017.01)
  *G06V 10/762*     (2022.01)
  *G06V 40/10*     (2022.01)

(52) U.S. Cl.
  CPC .............. *G06T 7/70* (2017.01); *A61B 5/0077* (2013.01); *A61B 5/1116* (2013.01); *A61B 5/1128* (2013.01); *G06T 7/50* (2017.01); *G06V*

*10/762* (2022.01); *G06V 40/10* (2022.01); *A61B 2576/00* (2013.01); *G06T 2207/30196* (2013.01); *G06T 2207/30232* (2013.01)

(58) Field of Classification Search
  None
  See application file for complete search history.

(56) References Cited

U.S. PATENT DOCUMENTS

| 10,740,600 | B2 * | 8/2020 | Watanabe | ............... G06T 7/194 |
| 2007/0200854 | A1 * | 8/2007 | Gordon | ............... G06V 40/166 |
| | | | | 345/474 |
| 2024/0119620 | A1 * | 4/2024 | Ishihara | ................. G06V 40/23 |

FOREIGN PATENT DOCUMENTS

| JP | 2009-506441 A | | 2/2009 |
| JP | 2020052476 A | * | 4/2020 |

OTHER PUBLICATIONS

International Search Report for PCT Application No. PCT/JP2021/021140, mailed on Aug. 3, 2021.

(Continued)

*Primary Examiner* — Delomia L Gilliard
(74) *Attorney, Agent, or Firm* — Sughrue Mion, PLLC

(57)     ABSTRACT

A posture estimation apparatus includes: a position calculation unit that calculates, for each joint of each of persons detected from image data, a provisional reference position of the person, based on a position of the joint and a displacement from the joint to a site serving as a reference for the person; and a posture estimation unit that determines a person to which the joint belongs based on the provisional reference position calculated for each joint detected.

15 Claims, 12 Drawing Sheets

(56)                     References Cited

OTHER PUBLICATIONS

Zhe Cao et al., "OpenPose: Realtime Multi-Person 2D Pose Estimation Using Part Affinity Fields," in IEEE Transactions on Pattern Analysis and Machine Intelligence, vol. 43, No. 1, Jan. 1, 2021, pp. 172-186.

Xingyi Zhou et al., "Objects as Points," arXiv:1904.07850, 2019.

English translation of Written opinion for PCT Application No. PCT/JP2021/021140, mailed on Aug. 3, 2021.

* cited by examiner

Fig.2
(a)
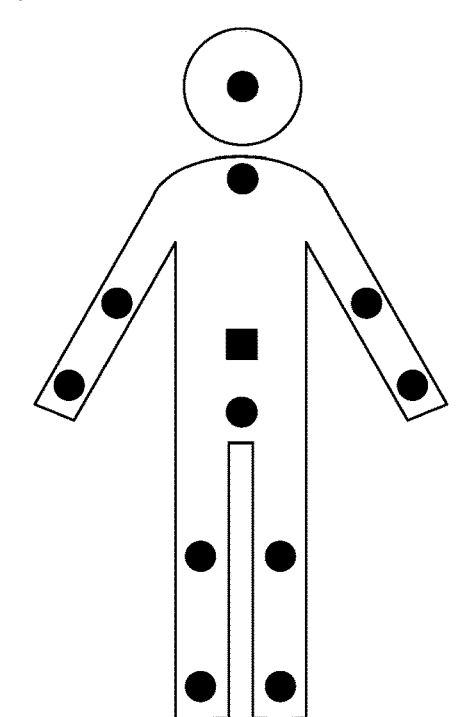
(b)
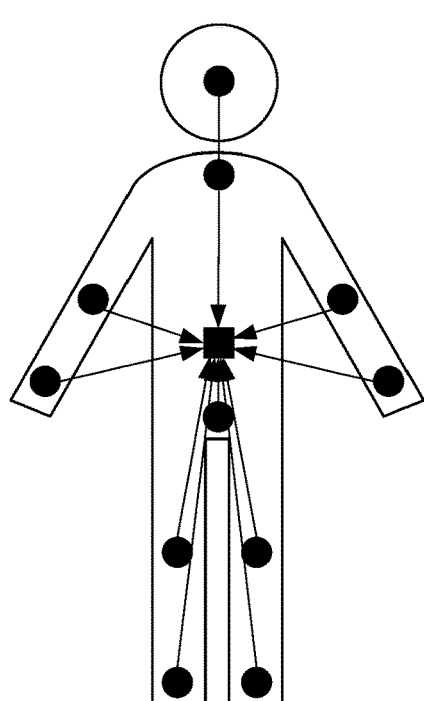
(c)
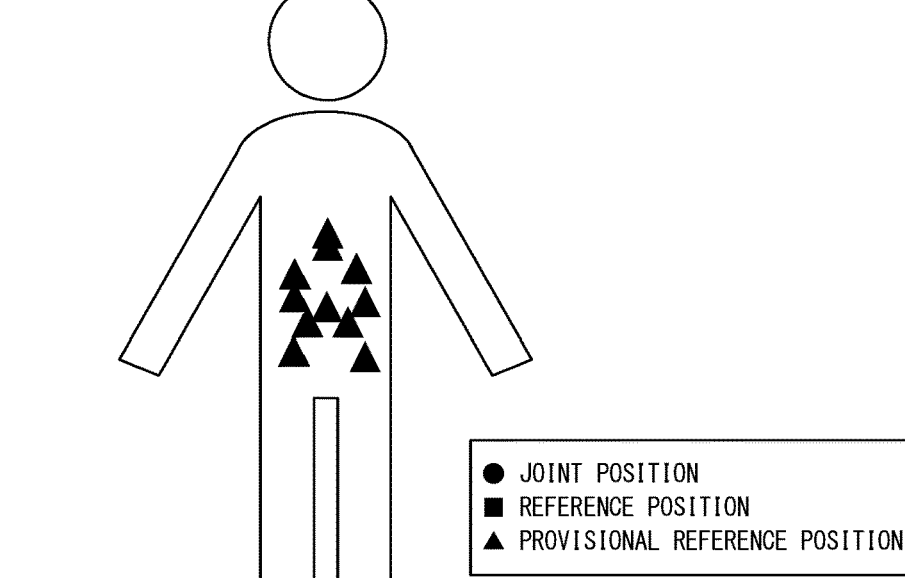
● JOINT POSITION
■ REFERENCE POSITION
▲ PROVISIONAL REFERENCE POSITION

Fig.3

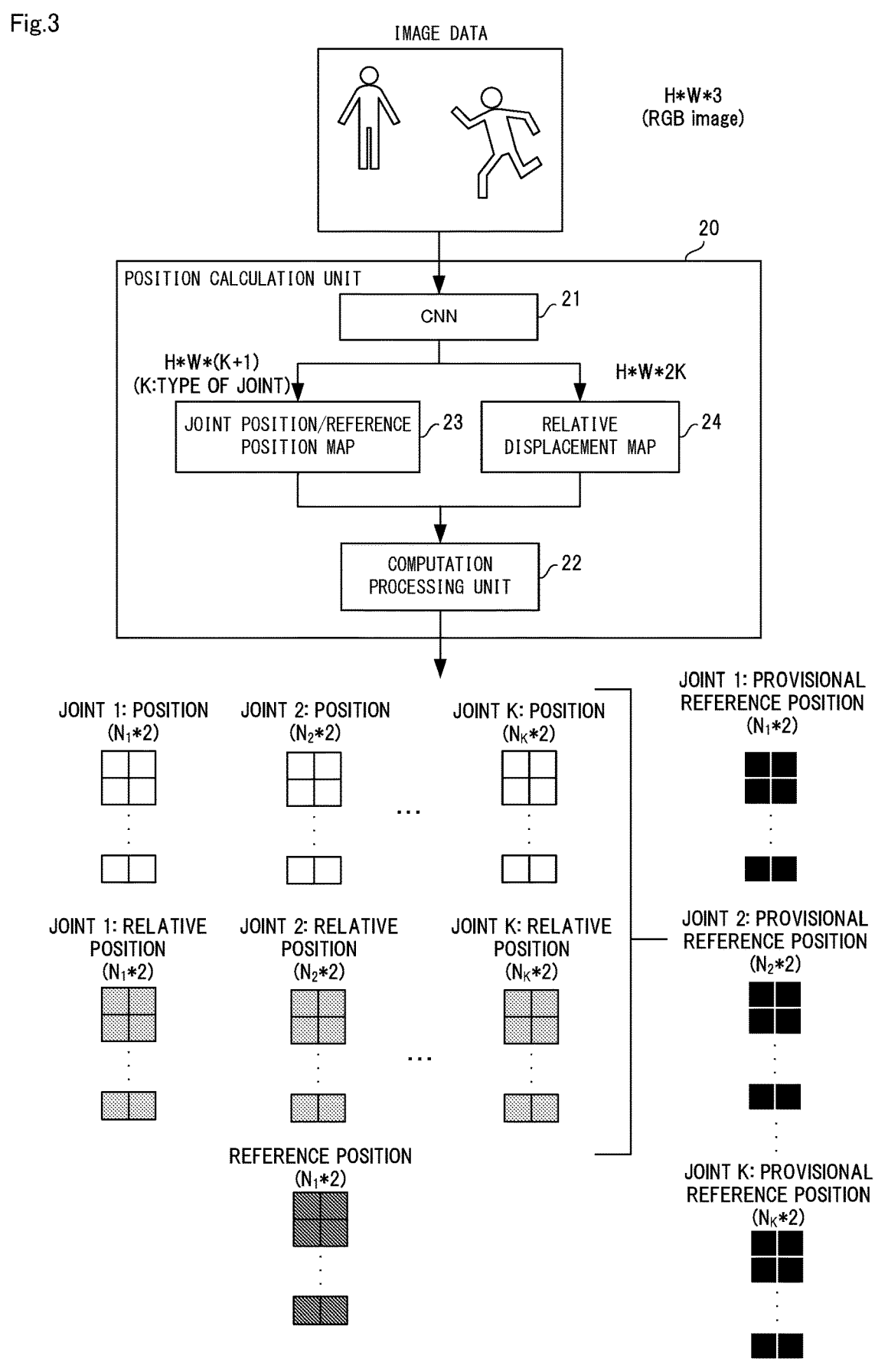

IMAGE DATA

H*W*3
(RGB image)

20

POSITION CALCULATION UNIT

CNN — 21

H*W*(K+1)
(K:TYPE OF JOINT)

H*W*2K

JOINT POSITION/REFERENCE
POSITION MAP — 23

RELATIVE
DISPLACEMENT MAP — 24

COMPUTATION
PROCESSING UNIT — 22

JOINT 1: POSITION
$(N_1*2)$

JOINT 2: POSITION
$(N_2*2)$

JOINT K: POSITION
$(N_K*2)$

...

JOINT 1: PROVISIONAL
REFERENCE POSITION
$(N_1*2)$

JOINT 1: RELATIVE
POSITION
$(N_1*2)$

JOINT 2: RELATIVE
POSITION
$(N_2*2)$

JOINT K: RELATIVE
POSITION
$(N_K*2)$

...

JOINT 2: PROVISIONAL
REFERENCE POSITION
$(N_2*2)$

REFERENCE POSITION
$(N_1*2)$

JOINT K: PROVISIONAL
REFERENCE POSITION
$(N_K*2)$

Fig.4
IMAGE DATA
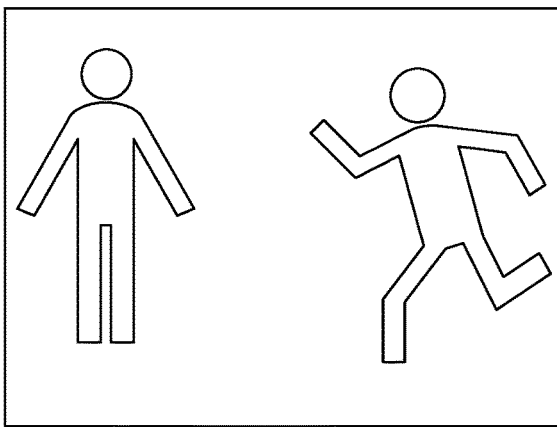
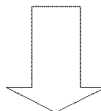
JOINT POSITION AND REFERENCE POSITION           RELATIVE DISPLACEMENT
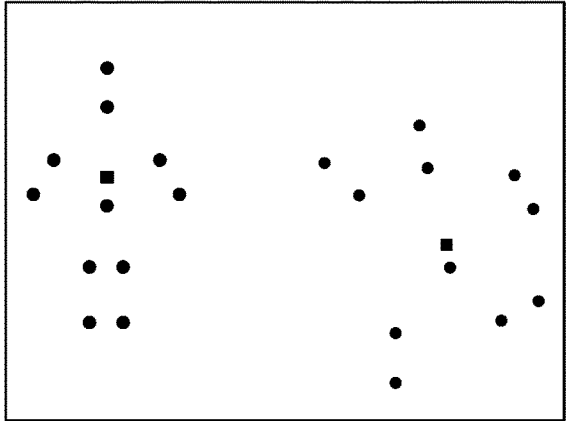 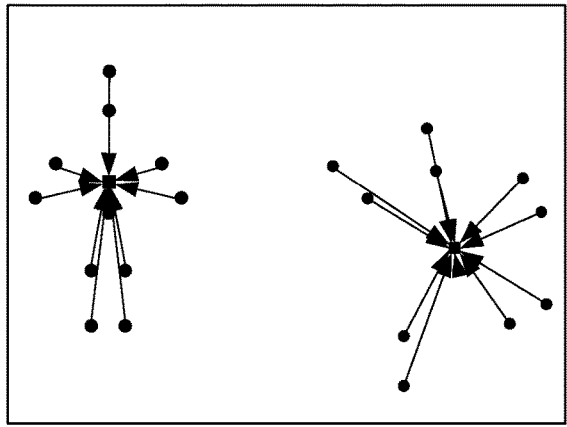
Determining person to which each
joint belongs using provisional
reference position.
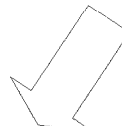
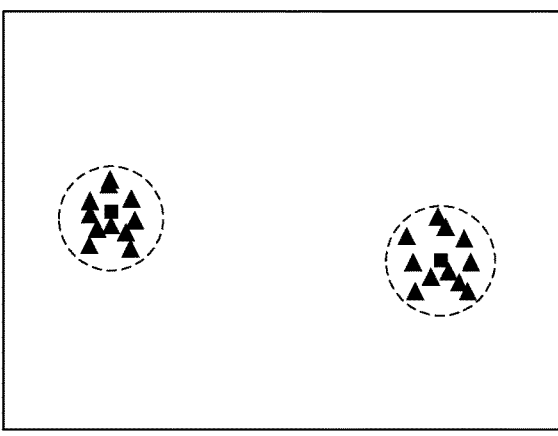
●   JOINT POSITION
■   REFERENCE POSITION
▲   PROVISIONAL REFERENCE POSITION

Fig.5

JOINT 1: PROVISIONAL
REFERENCE POSITION
$(N_1*2)$

JOINT 2: PROVISIONAL
REFERENCE POSITION
$(N_2*2)$

JOINT K: PROVISIONAL
REFERENCE POSITION
$(N_K*2)$

...

REFERENCE POSITION
$(N_1*2)$

CALCULATION OF DISTANCE MATRIX

DISTANCE MATRIX FOR
JOINT 1
$(N_b*N_1)$

DISTANCE MATRIX FOR
JOINT 2
$(N_b*N_2)$

DISTANCE MATRIX FOR
JOINT K
$(N_b*N_K)$

...

Associating each joint with reference position such that distance
between reference position and provisional reference position is the
lowest and is less than a set value.
(* NO DUPLICATION: Multiple joints of same type cannot be
associated with the same reference position.)

REFERENCE POSITION
$(N_1*2)$

JOINT 1: POSITION
$(N_1*2)$

JOINT 2: POSITION
$(N_2*2)$

JOINT K: POSITION
$(N_K*2)$

...

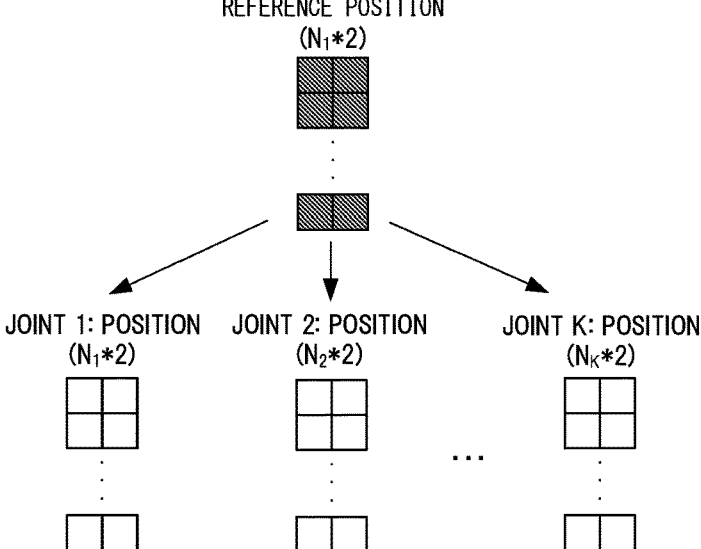

Fig.6
IMAGE DATA
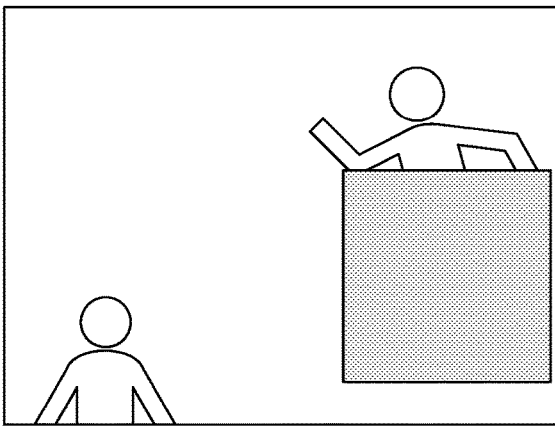
JOINT POSITION
RELATIVE DISPLACEMENT
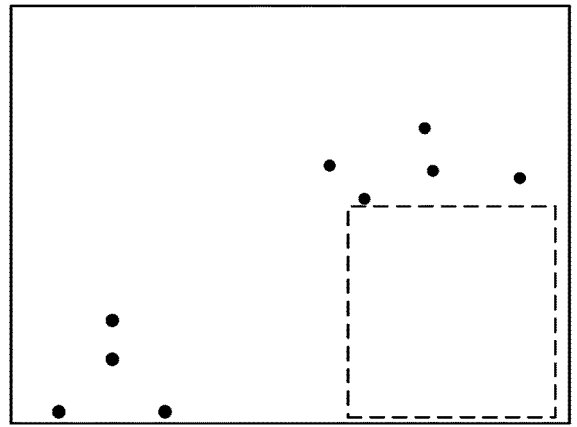
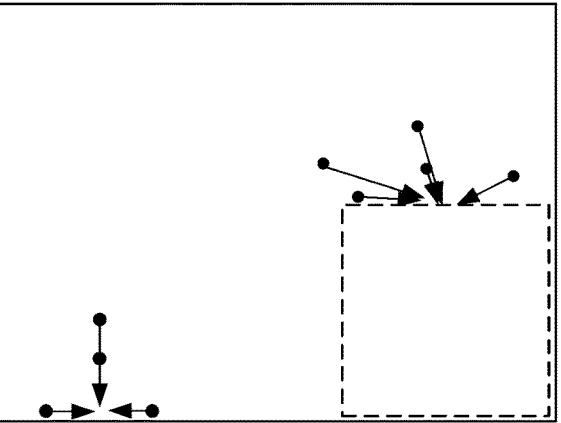
Determining which person each joint
belongs to by clustering.
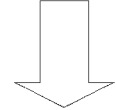
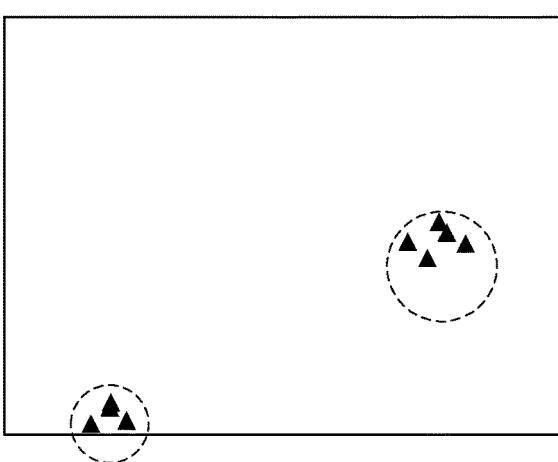

POSTURE ESTIMATION APPARATUS, POSTURE ESTIMATION METHOD, AND COMPUTER-READABLE RECORDING MEDIUM

This application is a National Stage Entry of PCT/JP2021/021140 filed on Jun. 3, 2021, the contents of all of which are incorporated herein by reference, in their entirety.

TECHNICAL FIELD

The invention relates to a posture estimation apparatus and a posture estimation method for estimating the posture of a person in an image, and further relates to a computer-readable recording medium for implementing the same.

BACKGROUND ART

Research for estimating the posture of a person from an image has been garnering attention in recent years. Such research is showing promise for use in the fields of video surveillance, sports, and the like. For example, in a station or the like where many people are present, it is conceivable that a person who commits a dangerous act can be identified by estimating the posture of each person from surveillance camera video. In addition, it is conceivable that products can be placed efficiently by analyzing the movement of employees in the store using video from surveillance cameras installed in the store.

Non-Patent Documents 1 and 2 disclose examples of systems that estimate the posture of a person. Specifically, the system disclosed in Non-Patent Document 1 first obtains image data output from a camera, and then estimates the joints of a person in an image and vector fields between the joints based on the obtained image data. The system disclosed in Non-Patent Document 1 then obtains the direction between the joints for each of sets of two adjacent joints.

Next, for each set of two adjacent joints, the system disclosed in Non-Patent Document 1 obtains an inner product of the direction obtained and the vector field estimated between those joints, and then calculates a confidence of the association between the joints based on the inner product. Then, the system disclosed in Non-Patent Document 1 identifies the joints to be associated based on the confidence, and estimates the posture of the persons.

The system disclosed in Non-Patent Document 2 first obtains image data output from a camera, inputs the obtained image data to a detector, and outputs a reference position of a person in the image and a relative position of each of joints from the reference position. Next, the system disclosed in Non-Patent Document 2 estimates the posture of the person in the image based on the reference position of the person that has been output and the relative position of each joint. The detector in this case is constructed through machine learning using images, and the reference position of people in the images and the relative positions of each joint, as training data.

LIST OF RELATED ART DOCUMENTS

Patent Document

NON PATENT DOCUMENT

Non-Patent Document 1: Z. Cao, G. Hidalgo, T. Simon, S.-E. Wei and Y. Sheikh, "OpenPose: Realtime Multi-Person 2D Pose Estimation Using Part Affinity Fields,"

in IEEE Transactions on Pattern Analysis and Machine Intelligence, vol. 43, No. 1, pp. 172-186, Jan. 1, 2021
Non-Patent Document 2: X. Zhou, D. Wang and P. Krahenbuhl, "Objects as Points," arXiv: 1904.07850, 2019.

SUMMARY OF INVENTION

Problems to be Solved by the Invention

Incidentally, the above-described systems disclosed in Non-Patent Documents 1 and 2 have a problem that if a part of the person subject to posture estimation is hidden by another person or an object in the image, the posture cannot be estimated accurately.

Assume, for example, that the right knee of the person subject to estimation is detected in the image, but the right ankle of that person is hidden by the right knee of another person and is not detected. In this case, with the system disclosed in Non-Patent Document 1, the right knee of the person subject to estimation is likely to be associated with the right ankle of the other person, and thus the posture cannot be estimated accurately.

Or, assume that the right ankle of the person subject to estimation is detected, but the right knee is not detected. In this case, the system disclosed in Non-Patent Document 1 cannot associate the right ankle of the person subject to estimation to the right knee. As such, even in this case, the system disclosed in Non-Patent Document 1 cannot estimate the posture accurately.

Furthermore, assume that in an image, a site serving as the reference position of the person subject to estimation is hidden by another person and is not detected. In this case, with the system disclosed in Non-Patent Document 2, the detector cannot accurately output the reference position of the person subject to estimation, which makes it difficult to estimate the posture accurately.

An example object of the invention is to provide a posture estimation apparatus, a posture estimation method, and a computer-readable recording medium capable of improving the accuracy of posture estimation when a part of a person subject to estimation is hidden.

Means for Solving the Problems

In order to achieve the above-described object, a posture estimation apparatus includes:

a position calculation unit that calculates, for each joint of each of persons detected from image data, a provisional reference position of the person, based on a position of the joint and a displacement from the joint to a site serving as a reference for the person; and a posture estimation unit that determines a person to which the joint belongs based on the provisional reference position calculated for each joint detected.

In order to achieve the above-described object, a posture estimation method includes:

a position calculation step of calculating, for each joint of each of persons detected from image data, a provisional reference position of the person, based on a position of the joint and a displacement from the joint to a site serving as a reference for the person; and a posture estimation step of determining a person to which the joint belongs based on the provisional reference position calculated for each joint detected.

In order to achieve the above-described object, a computer readable recording medium according to an example aspect of the invention is a computer readable recording medium that includes recorded thereon a program, the program including instructions that cause the computer to carry out:

a position calculation step of calculating, for each joint of each of persons detected from image data, a provisional reference position of the person, based on a position of the joint and a displacement from the joint to a site serving as a reference for the person; and a posture estimation step of determining a person to which the joint belongs based on the provisional reference position calculated for each joint detected.

Advantageous Effects of the Invention

As described above, according to the invention, it is possible to improving the accuracy of posture estimation when a part of a person subject to estimation is hidden.

BRIEF DESCRIPTION OF THE DRAWINGS

FIG. 2 is a diagram illustrating a position calculated by the position calculation unit, where FIG. 2(a) illustrates an example of the positions of joints, FIG. 2(b) illustrates an example of the relative position, and FIG. 2(c) illustrates an example of the provisional reference positions.

FIG. 3 is a diagram illustrating the specific configuration of and processing by the position calculation unit.

FIG. 4 is a diagram illustrating an overview of processing by the position calculation unit and the posture estimation unit.

FIG. 5 is a diagram illustrating specific processing performed by the posture estimation unit.

FIG. 6 is a diagram illustrating an overview of processing performed by the position calculation unit and the posture estimation unit when the reference position cannot be detected.

EXAMPLE EMBODIMENTS

First Example Embodiment

A posture estimation apparatus, a posture estimation method, and a program according to a first example embodiment will be described hereinafter with reference to FIGS. 1 to 8.

[Apparatus Configuration]

Figure 1:
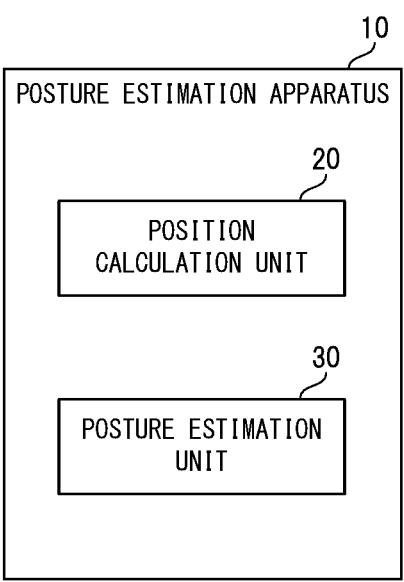
FIG. 1 is a block diagram illustrating the overall configuration of the posture estimation apparatus according to the first example embodiment.

First, the overall configuration of the posture estimation apparatus according to the first example embodiment will be described with reference to FIG. 1. FIG. 1 is a block diagram illustrating the overall configuration of the posture estimation apparatus according to the first example embodiment.

A posture estimation apparatus 10 according to the first example embodiment, illustrated in FIG. 1, is an apparatus for estimating the posture of a person in an image. As illustrated in FIG. 1, the posture estimation apparatus 10 includes a position calculation unit 20 and a posture estimation unit 30.

Based on the position of each of joints of persons detected from image data and a displacement (called a "relative displacement" hereinafter) from the joint to a site serving as a reference of a person (called a "reference site" hereinafter), the position calculation unit 20 calculates a provisional reference position of the person. For each joint detected, the posture estimation unit 30 determines the person to which the joint belongs based on the calculated provisional reference position.

As described above, in the first example embodiment, by using the position of each joint detected on the image data and the relative displacement from each joint to the reference site of a person (e.g., the abdomen, the neck, or the like), a provisional reference position is calculated for each joint, and the person to whom each joint belongs is determined by the provisional reference positions. In other words, even if the reference site of the person does not appear in the image data, as long as the relative displacements from the joints to the reference site are known, the joints and the person can be associated. As such, according to the first example embodiment, the accuracy of the posture estimation can be improved even when part of the person subject to estimation is hidden.

The configuration and functions of the position calculation unit 20 in the posture estimation apparatus 10 will be described in detail next with reference to FIGS. 2 and 3. FIG. 2 is a diagram illustrating a position calculated by the position calculation unit, where FIG. 2(a) illustrates an example of the positions of joints, FIG. 2(b) illustrates an example of the relative position, and FIG. 2(c) illustrates an example of the provisional reference positions. FIG. 3 is a diagram illustrating the specific configuration of and processing by the position calculation unit.

In the first example embodiment, the position calculation unit 20 detects, from the image data, the joints of a person and the reference site of the person, as illustrated in FIG. 2(a). Additionally, the position calculation unit 20 estimates the positions of the detected joints (called "joint positions" hereinafter) and the position of the detected reference site. The estimated position of the reference site here is not provisional, but is rather a true "reference position".

The target joints are the right wrist, the right elbow, the right ankle, the right knee, the left wrist, the left elbow, the left ankle, the left knee, and the like, and are set in advance. The reference site is also set in advance. The solar plexus, the base of the neck, and the like can be given as examples of the reference site. In FIGS. 2(a) and (b), joint positions are indicated by ●, and the reference position is indicated by ■.

Furthermore, in the first example embodiment, the position calculation unit 20 can also estimate the position of a site set in advance, such as the position of the head, in addition to the joint positions and the reference position. The position of the head is also indicated by ● in FIGS. 2(a) and (b). In the first example embodiment, the joint positions also include the position of the head. As indicated in FIG. 2(*b*), the position calculation unit 20 also estimates a displacement (x,y) from the joint to the reference site for each joint in the image, based on the image data.

The position calculation unit 20 then calculates a provisional reference position for each joint. The provisional reference position is a provisional position of the reference site of the person, estimated from the joint position of each joint. The provisional reference position may differ from joint to joint. Specifically, as illustrated in FIG. 2(*c*), the position calculation unit 20 calculates the provisional reference position by adding the coordinates of the joint position and the relative displacement for the joint, for each joint in the image.

In FIG. 2(*c*), the provisional reference positions are indicated by ▲. Note that in FIGS. 2(*a*) to (*c*), the position of the reference site (the reference position) does not match the provisional reference position for each joint because the joint position, the reference position, and the displacement are estimated through image processing. The image processing used in the first example embodiment will be described later.

The configuration of the position calculation unit 20 will be described in detail here. As illustrated in FIG. 3, in the first example embodiment, the position calculation unit 20 includes a convolutional neural network (CNN) 21 and a computation processing unit 22.

When image data of a person is input, the CNN 21 outputs a map 23 indicating an existence probability for the reference site and each joint of the person (called a "joint position/reference position map" hereinafter). Additionally, when the image data of the person is input, the CNN 21 also outputs a map 24 indicating the relative displacement for each joint of the person (called a "relative displacement map").

In the first example embodiment, the joint position/reference position map 23 is, for example, a two-dimensional heat map using density to represent the existence probability of a target. The relative displacement map 24 is a map storing the magnitude and orientation of the relative displacement in elements corresponding to the joint positions on the map. The CNN 21 is constructed by performing deep learning using images of extraction targets and labels indicating the extraction targets as training data.

When multiple people are present in the image data, the CNN 21 outputs the joint position/reference position map 23 for all of the joints in the image. Additionally, information indicating the site of the joint (the right elbow, the left elbow, or the like), or information indicating a site that serves as a reference, is added to each joint position/reference position map 23. Information indicating the sites of the corresponding joints is also added to the relative displacement map 24.

Note that there are cases where in the image data, a part of a person's body is shielded by an object, only a part of a person is displayed, and the like, and thus the reference sites for all or some of the people may not appear in the image data. In this case, the position calculation unit cannot detect the reference site, and therefore detects only the joints that appear in the image and estimates only the joint positions of the detected joints.

Using the joint position/reference position map 23, the computation processing unit 22 estimates the joint position of each joint and the reference position. Additionally, using the relative displacement map 24, the computation processing unit 22 estimates the relative displacement of each joint.

Specifically, each joint and the site serving as a reference are constituted by a plurality of pixels, and thus the computation processing unit 22 calculates coordinates (x,y) of each pixel constituting a joint position, the reference position, and the relative displacements, as illustrated in FIG. 3. In FIG. 3, one pixel is represented by two rectangles, where one rectangle corresponds to the x coordinate and the other to the y coordinate. Additionally, the computation processing unit 22 calculates the coordinates of each pixel of the provisional reference position using the coordinates of each pixel of the joint positions and relative displacements, as illustrated in FIG. 3.

Next, the functions of the posture estimation unit 30 when the reference site of a person is detected from the image data will be described in detail with reference to FIGS. 4 and 5. FIG. 4 is a diagram illustrating an overview of processing by the position calculation unit and the posture estimation unit. FIG. 5 is a diagram illustrating specific processing performed by the posture estimation unit.

As illustrated in FIG. 4, it is first assumed that the position calculation unit 20 has estimated the joint position of ● each joint, the reference position ■, and the relative displacement of each joint, and has calculated the provisional reference position ▲ for each joint. In this case, for each joint, the posture estimation unit 30 determines whether or not each joint belongs to the person corresponding to the detected reference position based on the provisional reference position ▲ and the detected reference position ■.

Specifically, as illustrated in FIG. 5, the posture estimation unit 30 first obtains a distance matrix between the provisional reference position and the estimated reference position for each detected joint. If a plurality of estimated reference positions are present, the posture estimation unit 30 obtains the distance matrix for each reference position, for each of the joints. The posture estimation unit 30 then associates each joint with one of the reference positions such that the distance between the estimated reference position and the provisional reference position is the lowest and is less than a set value. As a result, the person to which the joint belongs is determined for each joint.

Figure 7:
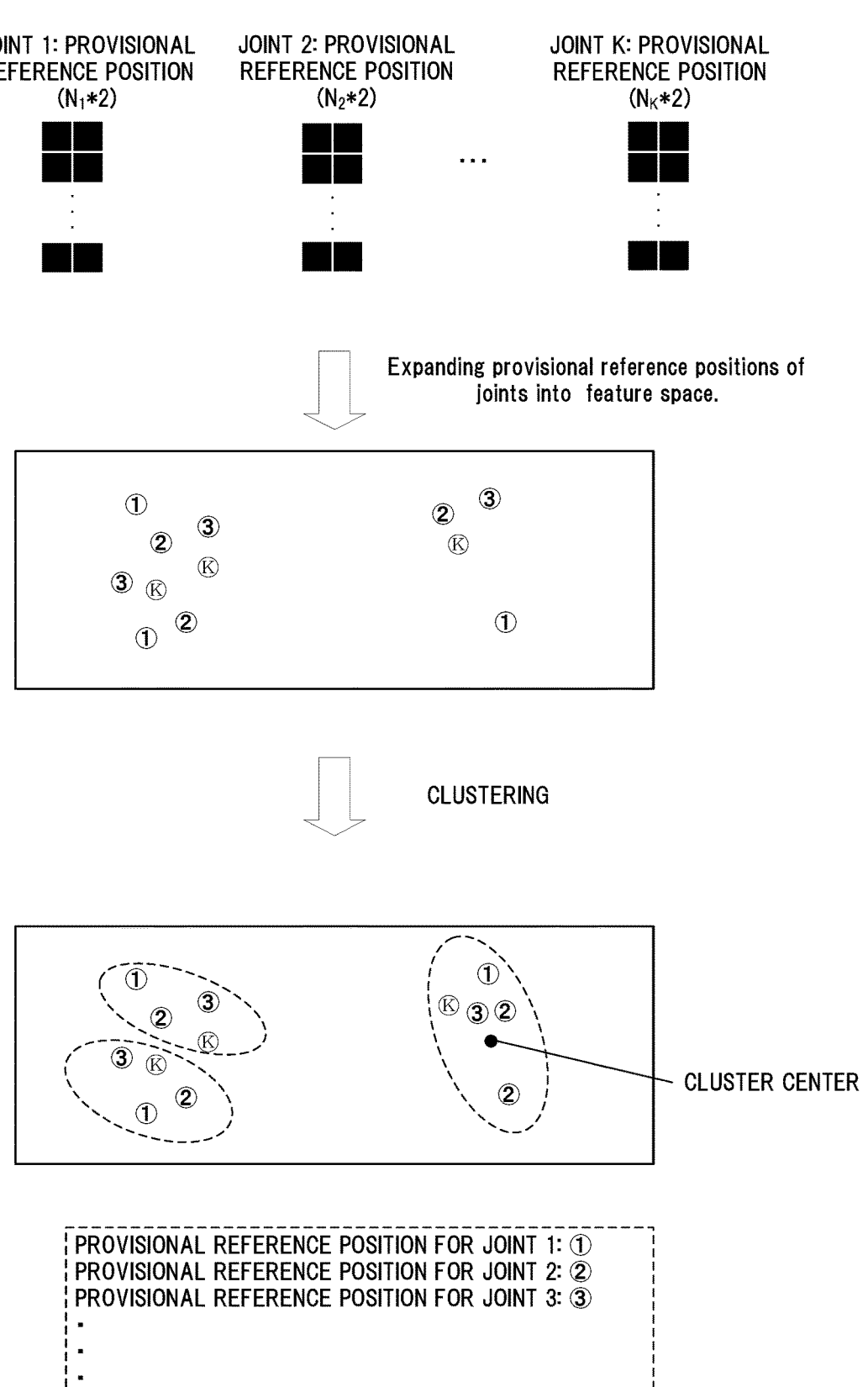
FIG. 7 is a diagram illustrating specific processing performed by the posture estimation unit when the reference position cannot be detected.

Furthermore, the functions of the posture estimation unit 30 when the reference site of the person is not detected from the image data will be described in detail with reference to FIGS. 6 and 7. FIG. 6 is a diagram illustrating an overview of processing performed by the position calculation unit and the posture estimation unit when the reference position cannot be detected. FIG. 7 is a diagram illustrating specific processing performed by the posture estimation unit when the reference position cannot be detected.

As illustrated in FIG. 6, it is assumed that in the image data, the body of one person is shielded by an object, only the upper body of another person is displayed, and the reference site of both people do not appear in the image data and therefore are not detected. In this case, the position calculation unit 20 detects each joint appearing in the image data, estimates the joint positions and relative displacements only for the detected joints, and calculates the provisional reference positions.

The reference position has not been estimated, and thus the posture estimation unit 30 performs clustering on the provisional reference positions of respective detected joints, and determines, based on the result of the clustering, the person to whom each joint belongs for each detected joint.

Specifically, as illustrated in FIG. 7, the posture estimation unit 30 expands the provisional reference positions of the detected joints into a feature space. The provisional reference position is expressed by two-dimensional coordinates, and thus the number of dimensions of the feature space in this case is two. Then, the posture estimation unit

30 performs clustering on the provisional reference positions expanded in the feature space through the following processing (a) to (e).

(a) A cluster center is determined at random.

(b) Clustering is performed through k-means using the determined cluster center.

(c) Whether the samples in the resulting cluster follow a Gaussian distribution is verified based on statistical hypothesis testing. This verification is based on the hypothesis that the samples in the cluster follow a Gaussian distribution.

(d) If the stated hypothesis is rejected by the verification in (c) above, the corresponding cluster is divided into two. On the other hand, if the stated hypothesis is not rejected by the verification in (c) above, the corresponding cluster is finalized.

(e) (b) to (d) above are iterated until the cluster is no longer divided in (d) above.

Additionally, the posture estimation unit 30 ensures that the provisional reference positions for a plurality of joints of the same type (e.g., the right wrist and the right wrist, or the like) are not included in the same cluster during the clustering. The posture estimation unit 30 then takes the joints in the provisional reference positions included in the same cluster as belonging to the same person.

The processing illustrated in FIGS. 6 and 7 is executed when a reference site is not detected for all the people in the image data. For example, when not even a single reference site is detected despite a plurality of joints being detected, the posture estimation unit 30 determines that a reference site has not been detected for all of the people in the image data, and executes the processing illustrated in FIGS. 6 and 7. Note that the posture estimation unit 30 can also execute the processing illustrated in FIGS. 6 and 7 when a reference site is detected for all of the people in the image data.

When the belonging persons are determined with respect to all of the joints, the posture estimation unit 30 estimates the posture of the person based on the positions of the joints belonging to that person, for each person. Specifically, the posture estimation unit 30 can estimate a final posture of the person by using a machine learning model that estimates information about all the joint positions from information about the joint positions of the person when some joints are missing due to being undetected or the like, for example.

[Apparatus Operations]

Figure 8:
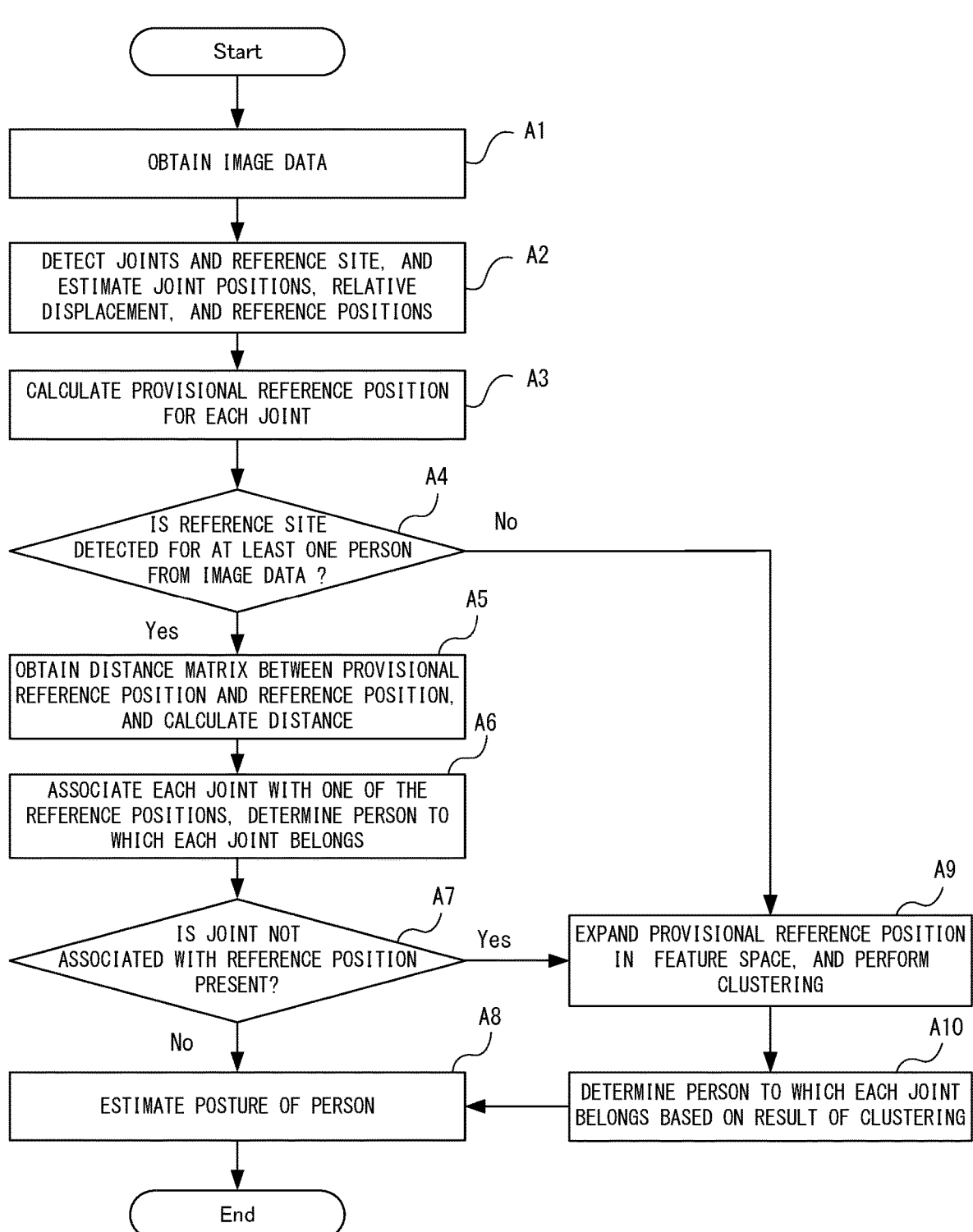
FIG. 8 is a flowchart illustrating operations of the posture estimation apparatus according to the first example embodiment.

Operations of the posture estimation apparatus 10 according to the first example embodiment will be described next with reference to FIG. 8. FIG. 8 is a flowchart illustrating operations of the posture estimation apparatus according to the first example embodiment. The following descriptions will refer to FIGS. 1 to 7 as appropriate. In the first example embodiment, a posture estimation method is implemented by operating the posture estimation apparatus 10. As such, the following descriptions of the operations of the posture estimation apparatus 10 will be given in place of descriptions of the posture estimation method according to the first example embodiment.

As illustrated in FIG. 8, first, the position calculation unit 20 obtains image data (step A1). The image data in step A1 may be image data output directly from an image capturing device such as a surveillance camera or the like, or may be image data stored in a storage device.

Next, the position calculation unit 20 detects the joints and the reference site of persons from the image data, and estimates the joint positions, the relative displacements, and the reference positions (step A2). Specifically, in step A2, when the image data obtained in step A1 is input, the CNN

21 outputs the joint position/reference position map 23 and the relative displacement map 24. Then, the computation processing unit 22 uses the joint position/reference position map 23 to estimate the joint positions and the reference position, and uses the relative displacement map 24 to estimate the relative displacement of each joint.

Next, the position calculation unit 20 calculates the provisional reference position for each joint using the joint positions and relative displacements estimated in step A2 (step A3). Specifically, in step A3, the position calculation unit 20 calculates the provisional reference position by adding the coordinates of the joint position and the relative displacement for the joint, for each joint, as illustrated in FIG. 2(c).

Next, in step A2, the posture estimation unit 30 determines whether a reference site is detected for at least one person from the image data (step A4). Specifically, when at least one reference position is estimated in step A2, the posture estimation unit 30 determines that a reference site is detected for at least one person.

If a reference site is detected for at least one person from the image data as a result of the determination in step A4, the posture estimation unit 30 executes the processing of steps A5 to A7.

In step A5, for each detected joint, the posture estimation unit 30 obtains a distance matrix between the provisional reference position and the estimated reference position, and furthermore calculates a distance from the distance matrix. If a plurality of reference positions estimated in step A2 are present, the posture estimation unit 30 obtains the distance matrix for each reference position, and calculates the distance, for each of the joints.

In step A6, the posture estimation unit 30 associates each joint with one of the reference positions such that the distance between the estimated reference position and the provisional reference position is the smallest and is less than a set value, and determines the person to which each joint belongs. The posture estimation unit 30 determines the person to which each joint belongs also on the condition that a plurality of joints of the same type (e.g., a right wrist and a right wrist, or the like) do not belong to the same person.

In step A7, the posture estimation unit 30 determines whether a joint not associated with a reference position is present. If there are no joints not associated with a reference position in step A7, the posture estimation unit 30 estimates the posture of the person based on the positions of the joints that belong to that person, for each person (step A8). A case where a joint that is not associated with a reference position in step A7 will be described later.

On the other hand, if a reference site is not detected for even person from the image data as a result of the determination in step A4, the posture estimation unit 30 executes the processing of steps A9 and A10.

In step A9, the posture estimation unit 30 expands the provisional reference positions for the joints in a feature space, and performs clustering on the provisional reference positions expanded in the feature space. Specifically, the posture estimation unit 30 performs the clustering through the above-described processing (a) to (e).

In step A10, the posture estimation unit 30 determines that the joints in the provisional reference positions included in the same cluster belong to the same person, and determines the person to which each joint belongs.

The posture estimation unit 30 executes step A8 after steps A9 and A10 are executed, and estimates the posture of the person based on the position of the joints belonging to that person, for each person.

If there is a joint that is not associated with a reference position in step A7, the posture estimation unit 30 executes steps A9 and A10 on the joint that is not associated with the reference position. As a result, a person is also determined for joints determined not to be associated with a reference position, and the posture estimation according to step A8 is further executed.

In this manner, the postures of persons in the image data are estimated when steps A1 to A10 are executed. When the image data is obtained from an image capturing device such as a surveillance camera or the like, steps A1 to A10 are executed each time the image data is output, or each time a set period of time passes, for example.

[Program]

It suffices for the program in the first example embodiment to be a program that causes a computer to carry out steps A1 to A10 illustrated in FIG. 8. By installing this program on a computer and executing the program, the posture estimation apparatus and the posture estimation method in the first example embodiment can be realized. In this case, one or more processors of the computer function and perform processing as the position calculation unit 20 and the posture estimation unit 30. Furthermore, besides a general-purpose PC, a smartphone and a tablet-type terminal device can be mentioned as examples of the computer.

The program in the first example embodiment may be executed by a computer system constructed from a plurality of computers. In this case, the computers may each function as one of the position calculation unit 20 and the posture estimation unit 30, for example.

Effects of First Example Embodiment

According to the first example embodiment as described thus far, even when a part of a person subject to the posture estimation is hidden in image data, the person to whom detected joints belong can be determined accurately, and the accuracy of the posture estimation can be improved.

Second Example Embodiment

Figure 9:
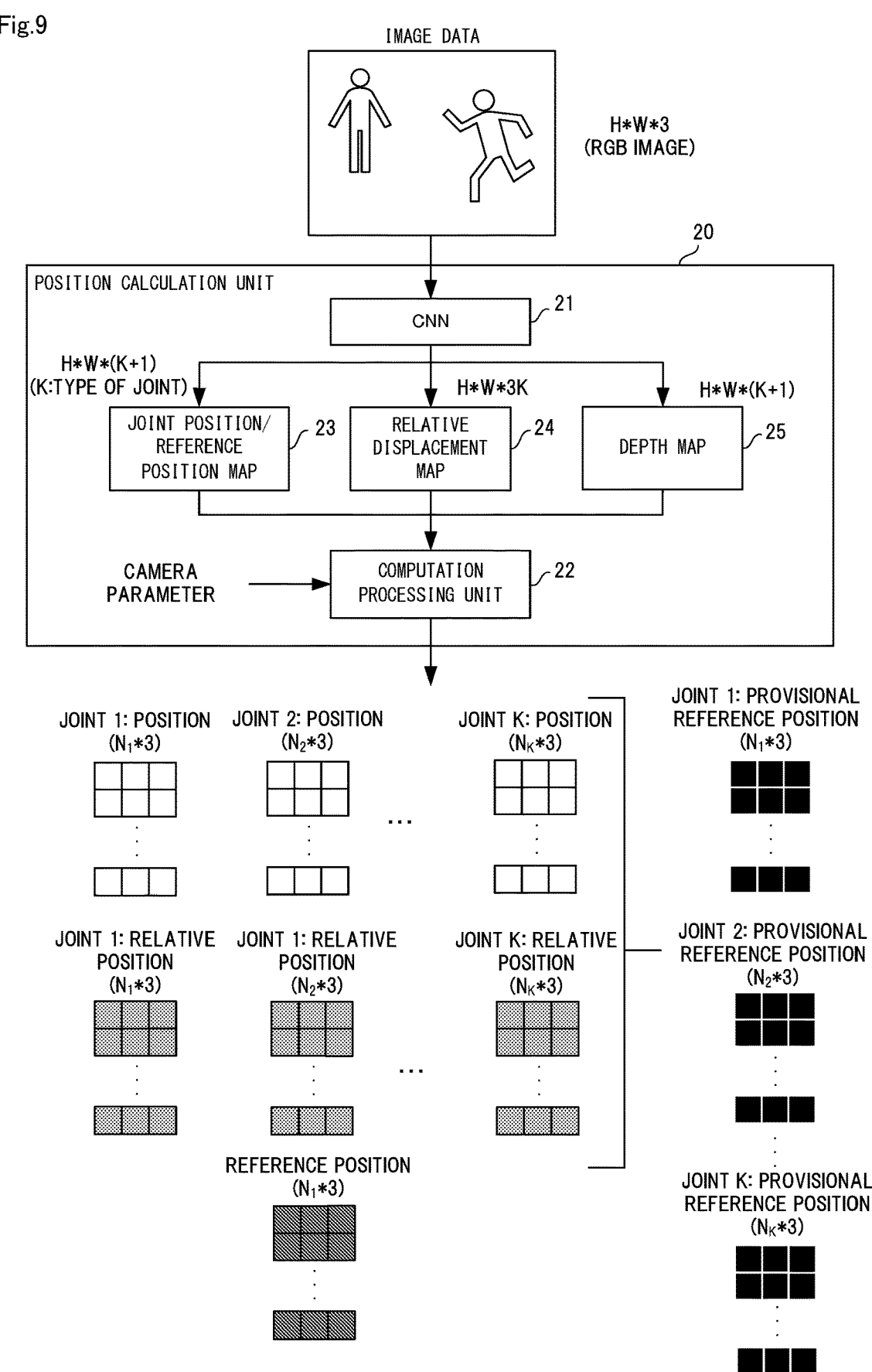
FIG. 9 is a diagram illustrating the specific configuration of and processing performed by the position calculation unit according to the second example embodiment.
Figure 10:
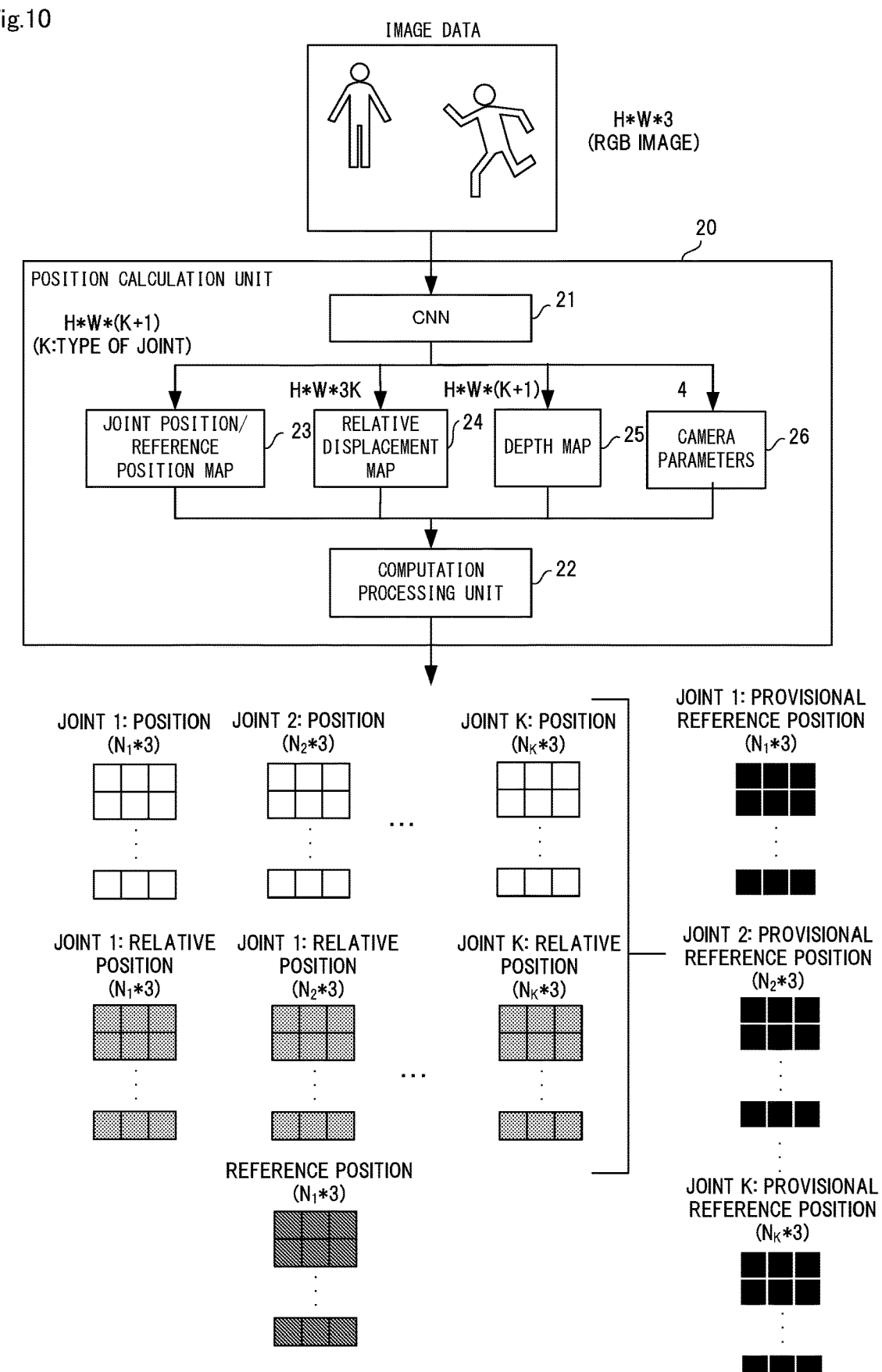
FIG. 10 is a diagram illustrating the specific configuration of and processing performed by the position calculation unit according to the first variation on the second example embodiment.
Figure 11:
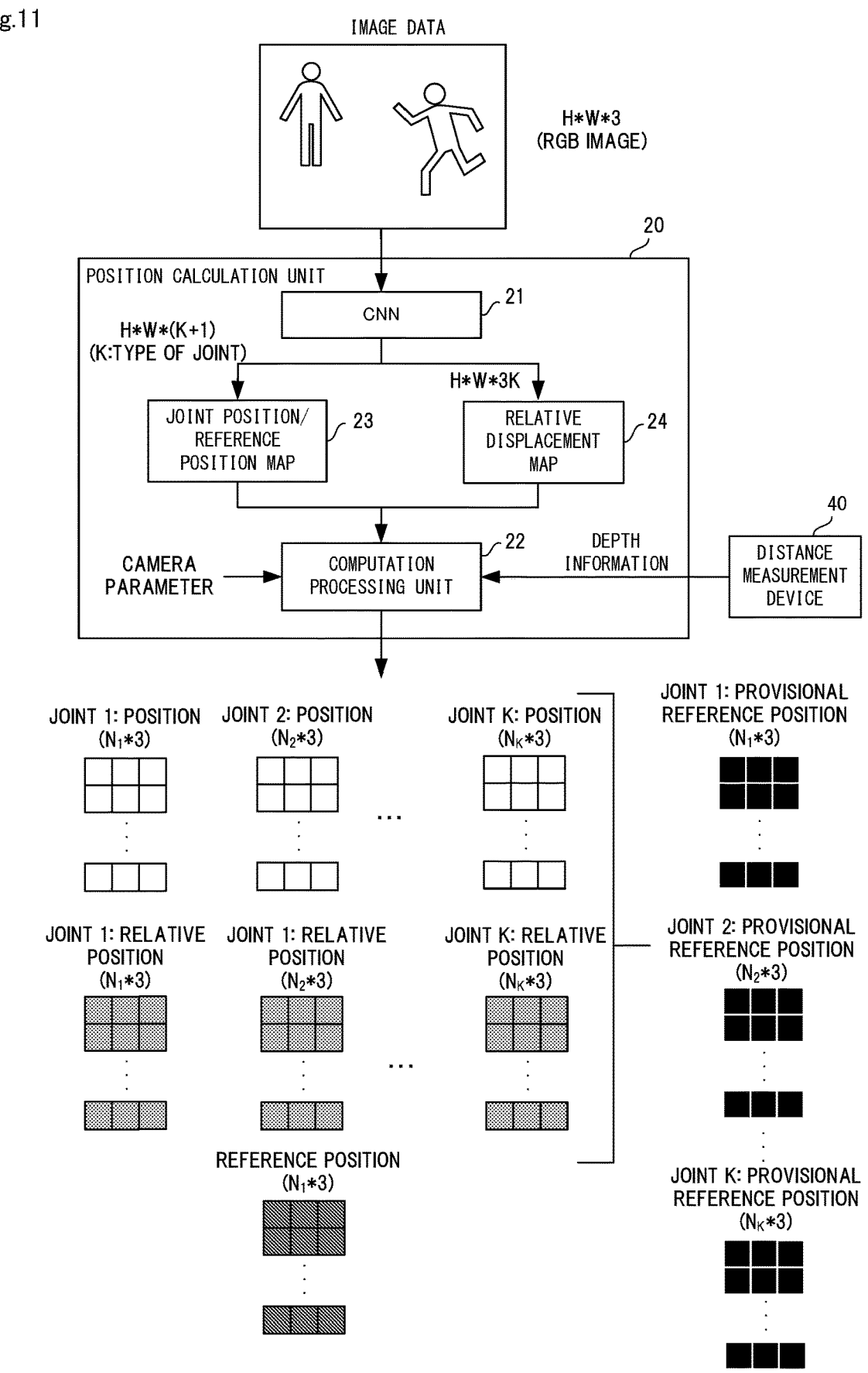
FIG. 11 is a diagram illustrating the specific configuration of and processing performed by the position calculation unit according to the second variation on the second example embodiment.

A posture estimation apparatus, a posture estimation method, and a program according to a second example embodiment will be described next with reference to FIGS. 9 to 11.

The posture estimation apparatus according to the second example embodiment has a configuration similar to that of the posture estimation apparatus according to the first example embodiment illustrated in FIG. 1, and includes the position calculation unit 20 and the posture estimation unit 30. However, in the second example embodiment, unlike the first example embodiment, the joint position of the detected joint and the relative displacement of each joint are expressed as three-dimensional coordinates. The following will mainly describe the differences from the first example embodiment.

The posture estimation apparatus according to the second example embodiment differs from the posture estimation apparatus according to the first example embodiment in terms of the functions of the position calculation unit 20. In the second example embodiment, the position calculation unit 20 estimates three-dimensional coordinates indicating the joint position and three-dimensional coordinates indicating the relative displacement for each joint using a depth of each detected joint and parameters of a camera that shot the image data. The position calculation unit also calculates three-dimensional coordinates indicating the provisional reference positions of a person based on three-dimensional coordinates indicating the estimated joint positions and three-dimensional coordinates indicating the relative displacements.

This point will be described with reference to FIG. 9. FIG. 9 is a diagram illustrating the specific configuration of and processing performed by the position calculation unit according to the second example embodiment. As illustrated in FIG. 9, in the second example embodiment as well, the position calculation unit 20 includes the CNN 21 and the computation processing unit 22.

In the second example embodiment, as in the first example embodiment, when image data of persons is input, the CNN 21 outputs the joint position/reference position map 23 and the relative displacement map 24 for the reference site of the persons and for each joint.

However, in the second example embodiment, the relative displacement map 24 stores the magnitude and direction of the relative displacements to the reference position in three dimensions in elements corresponding to the joint positions in the image on the map. In addition, in the second example embodiment, when image data is input, the CNN 21 also outputs a depth map 25 for each reference site and each joint of the persons. The depth map 25 stores a depth (distance) from the reference site or the joint to the camera that shot the image data in the element corresponding to the joint position in the image on the map. In the second example embodiment, the CNN 21 is constructed by performing deep learning using images of extraction targets, depths to the extraction targets, and labels indicating the extraction targets as training data.

In the second example embodiment, the computation processing unit 22 estimates the three-dimensional coordinates of the joint position of each joint, and the reference positions, using camera parameters of the camera, the joint position/reference position map 23, and the depth map 25. Additionally, the computation processing unit 22 estimates the three-dimensional coordinates of the relative displacement of each joint using the camera parameters of the camera, the joint position/reference position map 23, the relative displacement map 24 of the camera, and the depth map 25.

In the second example embodiment, the camera parameters are input from an external source or the like. The camera parameters are constituted by internal parameters of the camera and external parameters. The internal parameters are parameters used for coordinate conversion between the three-dimensional coordinates of the camera, which take the position of the camera as the origin, and two-dimensional coordinates in the image. The focal length of the camera, the location of center of the image, and the like can be given as examples of the internal parameters. The external parameters are parameters used for coordinate conversion between three-dimensional world coordinates, which are real-world coordinates, and the camera coordinates. The height of the mounting position of the camera, the angle of elevation of the camera, and the like can be given as examples of the external parameters.

In the second example embodiment, each joint and the site serving as a reference is constituted by a plurality of pixels. The computation processing unit 22 calculates three-dimensional coordinates (x,y,z) of each of the pixels constituting the joint positions, the reference position, and the relative displacements, as illustrated in FIG. 9. In FIG. 9, one pixel is represented by three rectangles, which correspond to the x coordinate, the y coordinate, and the z coordinate, respectively. Additionally, as illustrated in FIG. 9, the computation processing unit 22 calculates the three-dimensional coordinates for each of the pixels of the provisional reference position using the three-dimensional coordinates for each of the pixels of the joint positions in the relative displacements.

Similar to the first example embodiment, in the second example embodiment, the posture estimation unit 30 determines the person to which each joint belongs based on the provisional reference positions calculated for each of the detected joints.

However, in the second example embodiment, three-dimensional coordinates are obtained as the reference position and the provisional reference positions. Accordingly, when reference sites are detected for all the people from the image data, the posture estimation unit 30 determines the person to which each joint belongs by obtaining a three-dimensional distance matrix. Meanwhile, if the reference sites are not detected for all the people from the image data, the posture estimation unit 30 expands the provisional reference positions in a three-dimensional feature space and clusters the positions, after which the person to which each joint belongs is determined.

Additionally, in the second example embodiment too, the posture estimation apparatus executes steps A1 to A7 illustrated in FIG. 8. However, unlike the first example embodiment, in the second example embodiment, the position calculation unit 20 estimates the three-dimensional coordinates indicating the joint position and the three-dimensional coordinates indicating the relative displacement for each joint in step A2. Additionally, unlike the first example embodiment, the position calculation unit 20 calculates the three-dimensional coordinates indicating the provisional reference positions of the person in step A3. Note that in the second example embodiment, a posture estimation method according to the second example embodiment is implemented by operating the posture estimation apparatus according to the second example embodiment.

Furthermore, a program according to the second example embodiment may be any program that causes a computer to execute steps A1 to A7 illustrated in FIG. 8. The posture estimation apparatus and the posture estimation method according to the second example embodiment can be implemented by installing the program in a computer and executing the program.

(First Variation)

A first variation on the second example embodiment will be described here with reference to FIG. 10. FIG. 10 is a diagram illustrating the specific configuration of and processing performed by the position calculation unit according to the first variation on the second example embodiment. As illustrated in FIG. 10, in the first variation too, the position calculation unit 20 includes the CNN 21 and the computation processing unit 22.

However, in the first variation, when image data of a person is input, the CNN 21 also outputs camera parameters 26 of the camera that shot the image data, in addition to the joint position/reference position map 23, the relative displacement map 24, and the depth map 25. In the first variation, the CNN 21 is constructed by performing deep learning using images of extraction targets, depths to the extraction targets, labels indicating the extraction targets, and the camera parameters as training data.

Accordingly, in the first variation, using the parameters output by the CNN 21, the computation processing unit 22 estimates three-dimensional coordinates indicating the joint position and three-dimensional coordinates indicating the relative displacement for each joint, and calculates three-dimensional coordinates indicating provisional reference positions of the person using those items. According to the first variation, three-dimensional coordinates can be estimated and calculated without inputting camera parameters from an external source.

(Second Variation)

A second variation on the second example embodiment will be described next with reference to FIG. 11. FIG. 11 is a diagram illustrating the specific configuration of and processing performed by the position calculation unit according to the second variation on the second example embodiment. As illustrated in FIG. 10, in the second variation too, the position calculation unit 20 includes the CNN 21 and the computation processing unit 22.

In the second variation, similar to the example described in the first example embodiment, the CNN 21 outputs only the joint position/reference position map 23 and the relative displacement map 24. However, in the second variation, depth information and camera parameters are input into the position calculation unit 20.

The depth information is information specifying the depth of a target measured by a distance measurement device 40. In the second variation, the depth of an object in the image data input to the posture estimation apparatus is specified by the depth information. A device capable of obtaining depth information, such as a stereo camera, a Time-Of-Flight (TOF) camera, and Laser Imaging Detection and Ranging (LiDAR), can be given as a specific example of the distance measurement device 40.

In the second variation, the computation processing unit 22 estimates the three-dimensional coordinates of the joint position of each joint, and the reference position, using the camera parameters of the camera, the joint position/reference position map 23, and the depth information. The computation processing unit 22 also estimates the three-dimensional coordinates of the relative displacement of each joint using the camera parameters of the camera, the relative displacement map 24 of the camera, and the depth information. According to the second variation, three-dimensional coordinates can be estimated and calculated without having to output the depth of an object from the CNN 21.

Effects of Second Example Embodiment

As described thus far, according to the second example embodiment, the provisional reference position is calculated as three-dimensional coordinates, and thus even if a part of a person subject to posture estimation is hidden, the person to which joints belong can be determined more accurately, and the accuracy of the posture estimation can be further improved.

[Physical Configuration]

Figure 12:
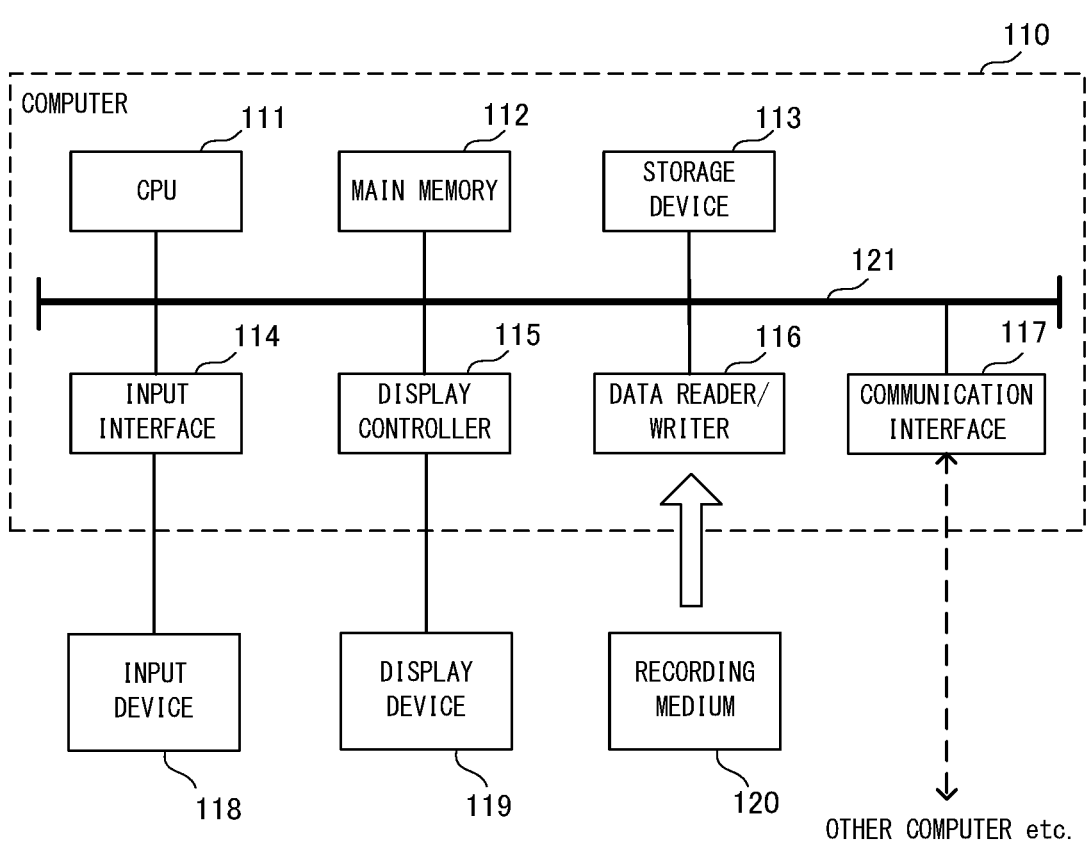
FIG. 12 is a block diagram illustrating an example of a computer that realizes the posture estimation apparatus according to the first and second example embodiment.

Using FIG. 12, the following describes a computer that realizes the posture estimation apparatus by executing the program according to the first and second example embodiment. FIG. 12 is a block diagram illustrating an example of a computer that realizes the posture estimation apparatus according to the first and second example embodiment.

As shown in FIG. 12, a computer 110 includes a CPU (Central Processing Unit) 111, a main memory 112, a storage device 113, an input interface 114, a display controller 115, a data reader/writer 116, and a communication interface 117. These components are connected in such a manner that they can perform data communication with one another via a bus 121.

The computer 110 may include a GPU (Graphics Processing Unit) or an FPGA (Field-Programmable Gate Array) in addition to the CPU 111, or in place of the CPU 111. In this case, the GPU or the FPGA can execute the program according to the example embodiment.

The CPU 111 deploys the program according to the example embodiment, which is composed of a code group stored in the storage device 113 to the main memory 112, and carries out various types of calculation by executing the codes in a predetermined order. The main memory 112 is typically a volatile storage device, such as a DRAM (dynamic random-access memory).

Also, the program according to the first and second example embodiment is provided in a state where it is stored in a computer-readable recording medium 120. Note that the program according to the first and second example embodiment may be distributed over the Internet connected via the communication interface 117.

Also, specific examples of the storage device 113 include a hard disk drive and a semiconductor storage device, such as a flash memory. The input interface 114 mediates data transmission between the CPU 111 and an input device 118, such as a keyboard and a mouse. The display controller 115 is connected to a display device 119, and controls display on the display device 119.

The data reader/writer 116 mediates data transmission between the CPU 111 and the recording medium 120, reads out the program from the recording medium 120, and writes the result of processing in the computer 110 to the recording medium 120. The communication interface 117 mediates data transmission between the CPU 111 and another computer.

Specific examples of the recording medium 120 include: a general-purpose semiconductor storage device, such as CF (CompactFlash®) and SD (Secure Digital); a magnetic recording medium, such as a flexible disk; and an optical recording medium, such as a CD-ROM (Compact Disk Read Only Memory).

Note that the posture estimation apparatus according to the first and second embodiment can also be realized by using items of hardware, such as a circuit that respectively correspond to the components rather than the computer in which the program is installed. Furthermore, a part of the posture estimation apparatus may be realized by the program, and the remaining part of the posture estimation apparatus may be realized by hardware.

A part or an entirety of the above-described example embodiment can be represented by (Supplementary Note 1) to (Supplementary Note 24) described below but is not limited to the description below.

(Supplementary Note 1)

A posture estimation apparatus comprising:

a position calculation unit that calculates, for each joint of each of persons detected from image data, a provisional reference position of the person, based on a position of the joint and a displacement from the joint to a site serving as a reference for the person; and a posture estimation unit that determines a person to which the joint belongs based on the provisional reference position calculated for each joint detected.

(Supplementary Note 2)

The posture estimation apparatus according to Supplementary Note 1, wherein for each joint of each of the persons, the position calculation unit estimates the position of the joint and the displacement for the joint, and calculates the provisional reference position of the person based on the position of the joint and the displacement for the joint which have been estimated.

(Supplementary Note 3)

The posture estimation apparatus according to Supplementary Note 1 or 2, wherein for each of the persons, the posture estimation unit estimates a posture of the person based on a position of the joint belonging to the person.

(Supplementary Note 4)

The posture estimation apparatus according to any one of Supplementary Notes 1 to 3, wherein when the site serving as a reference for each of the persons is detected from the image data, the posture estimation unit obtains, for each joint detected, a distance matrix between the provisional reference positions and a position of the site serving as a reference which has been detected, and determines a person to which the joint belongs using the distance matrix obtained.

(Supplementary Note 5)

The posture estimation apparatus according to Supplementary Note 4, wherein when a person for which the site serving as a reference has not been detected is present in the image data, the posture estimation unit performs clustering on the provisional reference position of each joint detected, and for each joint detected, determines a person to which the joint belongs based on a result of the clustering.

(Supplementary Note 6)

The posture estimation apparatus according to any one of Supplementary Notes 1 to 3, wherein the posture estimation unit performs clustering on the provisional reference position of each joint detected, and for each joint detected, determines a person to which the joint belongs based on a result of the clustering.

(Supplementary Note 7)

The posture estimation apparatus according to any one of Supplementary Notes 1 to 6, wherein the position of the joint and the displacement for the joint are expressed as three-dimensional coordinates.

(Supplementary Note 8)

The posture estimation apparatus according to Supplementary Note 2, wherein using a depth of each joint detected and a parameter of a camera that shot the image data, the position calculation unit estimates, for each joint, three-dimensional coordinates indicating a position of the joint and three-dimensional coordinates indicating the displacement for the joint, and calculates three-dimensional coordinates indicating the provisional reference position of the person based on the three-dimensional coordinates indicating the position of the joint and the three-dimensional coordinates indicating the displacement for the joint which have been estimated.

(Supplementary Note 9)

A posture estimation method comprising:

a position calculation step of calculating, for each joint of each of persons detected from image data, a provisional reference position of the person, based on a position of the joint and a displacement from the joint to a site serving as a reference for the person; and a posture estimation step of determining a person to which the joint belongs based on the provisional reference position calculated for each joint detected.

(Supplementary Note 10)

The posture estimation method according to Supplementary Note 9, wherein in the position calculation step, for each joint of each of the persons, the position of the joint and the displacement for the joint is estimated, and the provisional reference position of the person is calculated based on the position of the joint and the displacement for the joint which have been estimated.

(Supplementary Note 11)

The posture estimation method according to Supplementary Note 9 or 10, wherein in the posture estimation step, for each of the persons, a posture of the person is estimated based on a position of the joint belonging to the person.

(Supplementary Note 12)

The posture estimation method according to any one of Supplementary Notes 9 to 11, wherein when the site serving as a reference for each of the persons is detected from the image data, in the posture estimation step, for each joint detected, a distance matrix between the provisional reference positions and a position of the site serving as a reference which has been detected is obtained, and a person to which the joint belongs is determined using the distance matrix obtained.

(Supplementary Note 13)

The posture estimation method according to Supplementary Note 12, wherein when a person for which the site serving as a reference has not been detected is present in the image data, in the posture estimation step, clustering is performed on the provisional reference position of each joint detected, and for each joint detected, a person to which the joint belongs is determined based on a result of the clustering.

(Supplementary Note 14)

The posture estimation method according to any one of Supplementary Notes 9 to 11, wherein in the posture estimation step, clustering is performed on the provisional reference position of each joint detected, and for each joint detected, a person to which the joint belongs is determined based on a result of the clustering.

(Supplementary Note 15)

The posture estimation method according to any one of Supplementary Notes 9 to 14, wherein the position of the joint and the displacement for the joint are expressed as three-dimensional coordinates.

(Supplementary Note 16)

The posture estimation method according to Supplementary Note 10, wherein using a depth of each joint detected and a parameter of a camera that shot the image data, in the position calculation step, three-dimensional coordinates indicating a position of the joint and three-dimensional coordinates indicating the displacement for the joint are estimated for each joint, and three-dimensional coordinates indicating the provisional reference position of the person are calculated based on the three-dimensional coordinates indicating the position of the joint and the three-dimensional coordinates indicating the displacement for the joint which have been estimated.

(Supplementary Note 17)

A computer-readable recording medium that includes a program recorded thereon, the program including instructions that cause a computer to carry out:

a position calculation step of calculating, for each joint of each of persons detected from image data, a provisional reference position of the person, based on a position of the joint and a displacement from the joint to a site serving as a reference for the person; and a posture estimation step of determining a person to which the joint belongs based on the provisional reference position calculated for each joint detected.

(Supplementary Note 18)

The computer-readable recording medium according to Supplementary Note 17, wherein in the position calculation step, for each joint of each of the persons, the position of the joint and the displacement for the joint is estimated, and the provisional reference position of the person is calculated based on the position of the joint and the displacement for the joint which have been estimated.

(Supplementary Note 19)

The computer-readable recording medium according to Supplementary Note 17 or 18, wherein in the posture estimation step, for each of the persons, a posture of the person is estimated based on a position of the joint belonging to the person.

(Supplementary Note 20)

The computer-readable recording medium according to any one of Supplementary Notes 17 to 19, wherein when the site serving as a reference for each of the persons is detected from the image data, in the posture estimation step, for each joint detected, a distance matrix between the provisional reference positions and a position of the site serving as a reference which has been detected is obtained, and a person to which the joint belongs is determined using the distance matrix obtained.

(Supplementary Note 21)

The computer-readable recording medium according to Supplementary Note 20, wherein when a person for which the site serving as a reference has not been detected is present in the image data, in the posture estimation step, clustering is performed on the provisional reference position of each joint detected, and for each joint detected, a person to which the joint belongs is determined based on a result of the clustering.

(Supplementary Note 22)

The computer-readable recording medium according to any one of Supplementary Notes 17 to 19, wherein in the posture estimation step, clustering is performed on the provisional reference position of each joint detected, and for each joint detected, a person to which the joint belongs is determined based on a result of the clustering.

(Supplementary Note 23)

The computer-readable recording medium according to any one of Supplementary Notes 17 to 22, wherein the position of the joint and the displacement for the joint are expressed as three-dimensional coordinates.

(Supplementary Note 24)

The computer-readable recording medium according to Supplementary Note 18, wherein using a depth of each joint detected and a parameter of a camera that shot the image data, in the position calculation step, three-dimensional coordinates indicating a position of the joint and three-dimensional coordinates indicating the displacement for the joint are estimated for each joint, and three-dimensional coordinates indicating the provisional reference position of the person are calculated based on the three-dimensional coordinates indicating the position of the joint and the three-dimensional coordinates indicating the displacement for the joint which have been estimated.

Although the invention of the present application has been described above with reference to the example embodiment, the invention of the present application is not limited to the above-described example embodiment. Various changes that can be understood by a person skilled in the art within the scope of the invention of the present application can be made to the configuration and the details of the invention of the present application.

INDUSTRIAL APPLICABILITY

According to the invention, it is possible to improving the accuracy of posture estimation when a part of a person subject to estimation is hidden. The present invention is useful for systems that require estimation of a person's posture on image data, such as surveillance systems.

REFERENCE SIGNS LIST

10 Posture estimation apparatus
20 Position calculation unit
21 CNN
22 Computation processing unit
23 Joint position/reference position map
24 Relative displacement map
25 Depth map
26 Camera parameters
30 Posture estimation unit
40 Distance measurement device
110 Computer
111 CPU
112 Main memory
113 Storage device
114 Input interface
115 Display controller
116 Data reader/writer
117 Communication interface
118 Input device
119 Display device
120 Recording medium
121 Bus

What is claimed is:

1. A posture estimation apparatus comprising:
at least one memory storing instructions; and
at least one processor configured to execute the instructions to:
    calculate, for each joint of each of persons detected from image data, a provisional reference position of the person, based on a position of the joint and a displacement from the joint to a site serving as a reference for the person;
    determine a person to which the joint belongs based on the provisional reference position calculated for each joint detected; and
    in a case where the site serving as a reference for each of the persons is detected from the image data, obtain, for each joint detected, a distance matrix between the provisional reference positions and a position of the site serving as a reference which has been detected, and determine a person to which the joint belongs using the distance matrix obtained.

2. The posture estimation apparatus according to claim 1, wherein the at least one processor is further configured to execute the instructions to, for each joint of each of the persons, estimate the position of the joint and the displacement for the joint, and calculate the provisional reference position of the person based on the position of the joint and the displacement for the joint which have been estimated.

3. The posture estimation apparatus according to claim 2, wherein the at least one processor is further configured to execute the instructions to, using a depth of each joint detected and a parameter of a camera that shot the image data, estimate, for each joint, three-dimensional coordinates indicating a position of the joint and three-dimensional coordinates indicating the displacement for the joint, and calculate three-dimensional coordinates indicating the provisional reference position of the person based on the three-dimensional coordinates indicating the position of the joint and the three-dimensional coordinates indicating the displacement for the joint which have been estimated.

4. The posture estimation apparatus according to claim 1, wherein the at least one processor is further configured to execute the instructions to estimate, for each of the persons, a posture of the person based on a position of the joint belonging to the person.

5. The posture estimation apparatus according to claim 1, wherein the at least one processor is further configured to execute the instructions to perform clustering on the provisional reference position of each joint detected, and for each joint detected, determine a person to which the joint belongs based on a result of the clustering.

6. The posture estimation apparatus according to claim 1, wherein the position of the joint and the displacement for the joint are expressed as three-dimensional coordinates.

7. The posture estimation apparatus according to claim 1, wherein the at least one processor is further configured to execute the instructions to, in a case where a person for which the site serving as a reference has not been detected is present in the image data, perform clustering on the provisional reference position of each joint detected, and for each joint detected, determine a person to which the joint belongs based on a result of the clustering.

8. A posture estimation method comprising:
calculating, for each joint of each of persons detected from image data, a provisional reference position of the person, based on a position of the joint and a displacement from the joint to a site serving as a reference for the person;
determining a person to which the joint belongs based on the provisional reference position calculated for each joint detected; and
in a case where the site serving as a reference for each of the persons is detected from the image data, in the determining of the person, for each joint detected, a distance matrix between the provisional reference positions and a position of the site serving as a reference which has been detected is obtained, and a person to which the joint belongs is determined using the distance matrix obtained.

9. The posture estimation method according to claim 8, wherein in the calculating the provisional reference position, for each joint of each of the persons, the position of the joint and the displacement for the joint is estimated, and the provisional reference position of the person is calculated based on the position of the joint and the displacement for the joint which have been estimated.

10. The posture estimation method according to claim 9, wherein using a depth of each joint detected and a parameter of a camera that shot the image data, in the calculating the provisional reference position, three-dimensional coordinates indicating a position of the joint and three-dimensional coordinates indicating the displacement for the joint are estimated for each joint, and three-dimensional coordinates indicating the provisional reference position of the person are calculated based on the three-dimensional coordinates indicating the position of the joint and the three-dimensional coordinates indicating the displacement for the joint which have been estimated.

11. The posture estimation method according to claim 8, wherein in the determining the person, for each of the persons, a posture of the person is estimated based on a position of the joint belonging to the person.

12. The posture estimation method according to claim 8, wherein in the determining the person, clustering is performed on the provisional reference position of each joint detected, and for each joint detected, a person to which the joint belongs is determined based on a result of the clustering.

13. The posture estimation method according to claim 8, wherein the position of the joint and the displacement for the joint are expressed as three-dimensional coordinates.

14. The posture estimation method according to claim 8, wherein in a case where a person for which the site serving as a reference has not been detected is present in the image data, in the determining the person, clustering is performed on the provisional reference position of each joint detected, and for each joint detected, a person to which the joint belongs is determined based on a result of the clustering.

15. A non-transitory computer-readable recording medium that includes a program recorded thereon, the program including instructions that cause a computer to:

calculate, for each joint of each of persons detected from image data, a provisional reference position of the person, based on a position of the joint and a displacement from the joint to a site serving as a reference for the person;

determine a person to which the joint belongs based on the provisional reference position calculated for each joint detected; and in a case where the site serving as a reference for each of the persons is detected from the image data, in the determining of the person, for each joint detected, a distance matrix between the provisional reference positions and a position of the site serving as a reference which has been detected is obtained, and a person to which the joint belongs is determined using the distance matrix obtained.

* * * * *